Dec. 1, 1964 T. HUSTON Plant Pat. 2,458
PEACH TREE
Filed Aug. 29, 1963
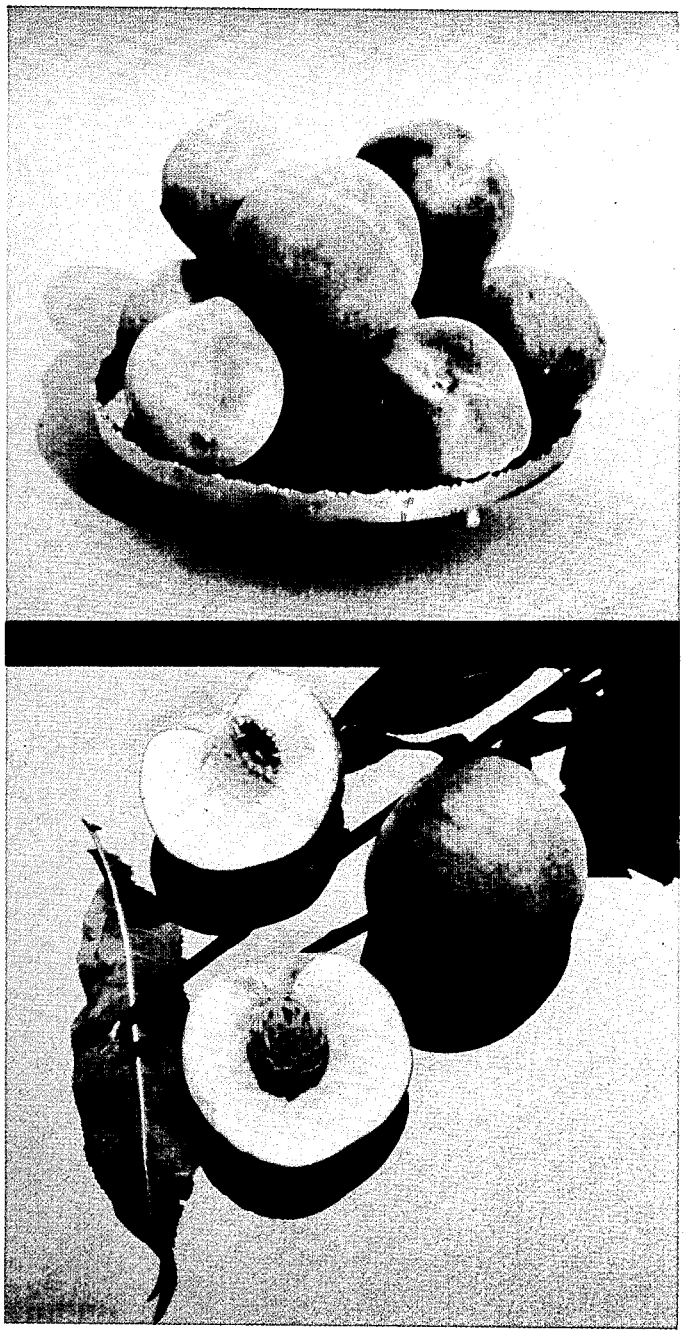
Inventor.
Tom Huston
By: Robb & Robb
Attorneys

United States Patent Office

Plant Pat. 2,458
Patented Dec. 1, 1964

2,458
PEACH TREE

Tom Huston, Miami, Fla., assignor to Peaches of Florida, Inc., Balm, Fla., a corporation of Florida

Filed Aug. 29, 1963, Ser. No. 305,568
1 Claim. (Cl. Plt.—43)

The present invention relates to a new and distinct variety of peach tree of the yellow-fleshed, freestone, fruit-bearing type, which was originated by me by crossing the peach variety known as "Okinawa" (unpatented) with the nectarine variety known as "Palomar" (Plant Patent No. 1,652).

The primary objective of this breeding was to produce a new peach variety which would be suitable for growing market fruit in central Florida where the average winter temperatures range around 350 to 400 hours below 45° F. In the past, it has not been feasible or profitable to grow peaches farther South than the borderline between the States of Georgia and Florida. Even in south Georgia, only a few early peach varieties have been successful and profitable, the most notable of which is the variety "Springtime" (Plant Patent No. 1,268). In the even more semi-tropical Florida area, the only peach varieties which will thrive are the old varieties "Okinawa" and "Red Ceylon" (unpatented), but even these two old varieties are unsatisfactory by reason of the fact that the fruit is of very poor quality and unmarketable, and therefore not suitable for commercial crops.

As the result of the aforementioned breeding, my principal objective has been fully achieved, along with other desirable improvements, as evidenced by the following unique combination of characteristics which are outstanding in the new variety and which distinguish it from its parents, as well as from all other varieties of which I am aware:

(1) Good production of firm, yellow-fleshed fruit of the freestone type, and of good color, shape and size, as well as good flavor and shipping qualities;

(2) An early ripening habit of the fruit, averaging about eighty days from bloom to ripe fruit, with a picking date at the shipping stage ranging over the last week or ten days in April in central Florida; and (3) A low winter chilling requirement, requiring only about 325 hours of chilling below 45° F., with consequent suitability for commercial use in southern latitudes of the United States as far south as central Florida.

A sexual reproduction of the new variety by both budding and grafting at Gainesville, Florida, shows that the foregoing characteristics and distinctions come true to form and are established and transmitted through succeeding propagations.

The accompanying drawing shows typical specimens of the foliage and fruit of my new variety, with both the upper and lower surfaces of the foliage being illustrated, as well as both exterior and sectional views of the fruit being shown, all as depicted in color as nearly true as it is reasonably possible to make the same in a color illustration of this character.

The following is a detailed description of my new variety, as based upon observations of specimens grown at Gainesville, Florida, with color terminology in accordance with Nickerson's Color Fan, published by Munsell Color Company, Inc., of Baltimore, Maryland, except where general color terms of ordinary dictionary significance are obvious:

*Tree*

Habit: Normal.
Fruit production: Good.
Growth: Vigorous.

Leaves:
- *Size.*—Length—from about 5 to 6 inches long. Width—from about 1 inch to 1⅜ inches wide.
- *Shape.*—Lanceolate, with apex acuminate.
- *Color.*—Upper surface—near Moderate Olive Green, Plate 2.5GY 5/5. Under surface—near Strong Yellow Green, Plate 2.5GY 6/8.
- *Petiole.*—Medium length.
- *Margin.*—Finely serrate.

*Flowers*

Blooming period: Early February in central Florida.
Size: Very small; average size from about ⅝ inch to ¾ inch in diameter.
Petalage: Single; usually 5 petals.
Color: Light pink, corresponding to near Moderate Pink, Plate 2.5R 8/5, with near white area in center of petals and extending to base.

*Fruit*

Ripening period: Early; ripens in about 80 days from bloom, and usually being shipping ripe about the last week or ten days of the month of April in central Florida.
Size: From about 2 inches to 2⅜ inches.
Form: Nearly round.
Suture: Usually a shallow line extending from base to apex, with slight depression near pistil point.
Base: Rounded.
Apex: Short.
Skin:
- *Thickness.*—Medium.
- *Color.*—Highly colored with dark red blush corresponding to near Moderate Red, Plate 2.5R 4/10 over good yellow ground color.

Flesh:
- *Quality.*—Good.
- *Flavor.*—Delectable flavor best described as a tangy blend of sweetness and acidity.
- *Color.*—New Pale Orange Yellow, Plate 7.5YR 9/4.

Stone:
- *Tenacity to flesh.*—Free.
- *Size.*—Length—about 1 inch. Width—about ¾ inch. Thickness—about ⅝ inch.
- *Form.*—Obovate.
- *Base.*—Rounded.
- *Apex.*—Sharply acute.
- *Sides.*—Approximately equal; furrowed and pitted throughout.
- *Color.*—Near Moderate Orange Yellow, Plate 7.5YR 8/8.

I claim:

A new and distinct variety of peach tree of the yellow-fleshed, freestone, fruit-bearing type, substantially as herein shown and described, characterized particularly as to novelty by the unique combination of good production of firm fruit of good color, shape and size and good flavor and shipping qualities, an early ripening habit of the fruit, averaging about eighty days from bloom, with a picking date at shipping stage occurring during the last week or ten days in the month of April in central Florida, and a low winter chilling requirement, requiring only about 325 hours of winter chilling below 45° F., with consequent suitability for commercial use in southern latitudes of the United States as far south as central Florida.

No references cited.

ABRAHAM G. STONE, *Primary Examiner.*